United States Patent [19]

Löffler et al.

[11] Patent Number: 6,140,094
[45] Date of Patent: Oct. 31, 2000

[54] PROTEIN WITH PHOSPHOLIPASE ACTIVITY

[75] Inventors: Fridolin Löffler, Bensheim; Gerald Jungschaffer, Alsbach-Hähnlein; Quoc Nguyen Khanh, Reichelsheim; Erwin Schuster, Bensheim; Bruno Sprössler, Rossdorf; Sabine Wolf, Otzberg, all of Germany

[73] Assignee: Rohm GmbH, Darmstadt, Germany

[21] Appl. No.: 09/142,469

[22] PCT Filed: Jan. 8, 1998

[86] PCT No.: PCT/EP98/00081

§ 371 Date: Sep. 8, 1998

§ 102(e) Date: Sep. 8, 1998

[87] PCT Pub. No.: WO98/31790

PCT Pub. Date: Jul. 23, 1998

[30] Foreign Application Priority Data

Jan. 16, 1997 [DE] Germany ............... 197 01 348

[51] Int. Cl.[7] .............. C12N 9/20; C12N 1/20; C12N 15/00; C07H 21/04; C07K 1/00
[52] U.S. Cl. ............ 435/198; 435/252.3; 435/320.1; 435/134; 435/913; 435/917; 530/350; 536/23.2; 536/23.74
[58] Field of Search ............... 435/198, 252.3, 435/320.1, 134, 913, 917; 530/350; 536/23.2, 23.74

[56] References Cited

FOREIGN PATENT DOCUMENTS 0 575 133  6/1993  European Pat. Off. .
0 808 903  11/1997 European Pat. Off. .
95/22615   8/1995  WIPO .
97/05219   2/1997  WIPO .

OTHER PUBLICATIONS

Process Biochemistry. 30(5) : 393–401, 1995.

*Primary Examiner*—Ponnathapu Achutamurthy
*Assistant Examiner*—Tekchand Saidha
*Attorney, Agent, or Firm*—Burns, Doane, Swecker & Mathis, L.L.P.

[57] ABSTRACT

This invention relates to a protein having phospholipase activity, which is characterised in that it has the mature sequence of Aspergillus lysophospholipase or a sequence derived therefrom and that it may be cleaved at at least one site, wherein, in the event of cleavage, the restriction fragments are optionally either linked by means of at least one bond cleavable under reducing conditions or at least one of the unlinked restriction fragments has phospholipase activity, and to a process for the production of this protein by fermenting a suitably transformed lysophospholipase-producing host organism in a suitable culture medium and isolating the protein having phospholipase activity from the cell-free culture filtrate, wherein fermentation is performed in the acidic to slightly alkaline range.

10 Claims, 2 Drawing Sheets

FIG. 1

PROCESSING OF THE LYSOPHOSPHOLIPASE GENE
FROM *ASPERGILLUS* AND ISOLATION OF THE PHOSPHOLIPASE

LPL
SVSTS _____ EASTTMLLF _____

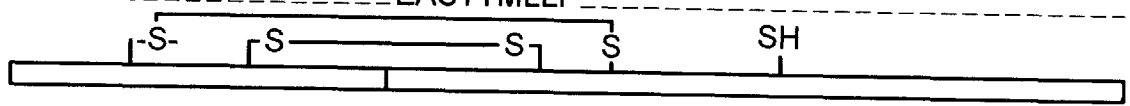

"LIGHT" CHAIN         "HEAVY" CHAIN
- IN SDS GEL WITH AND WITHOUT REDUCTION: APPROX. 36 kDa
- ONLY ONE SEQUENCE

PL WITHOUT REDUCTION

SVSTS _____
EASTTMLLEF _____

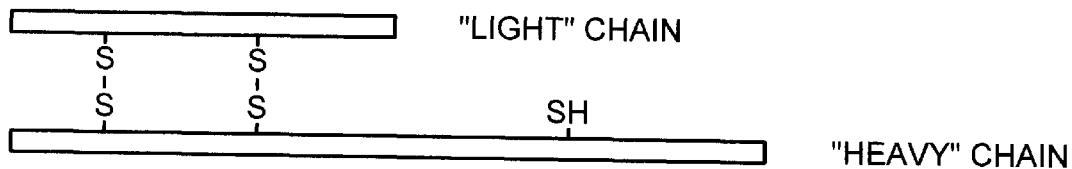

- IN SDS GEL WITH REDUCTION APPROX. 30 kDA
  AND WITHOUT REDUCTION APPROX. 36 kDa
- DOUBLE SEQUENCE, 1:1 RATIO

PL WITH REDUCTION

EASTTMLLEF _____

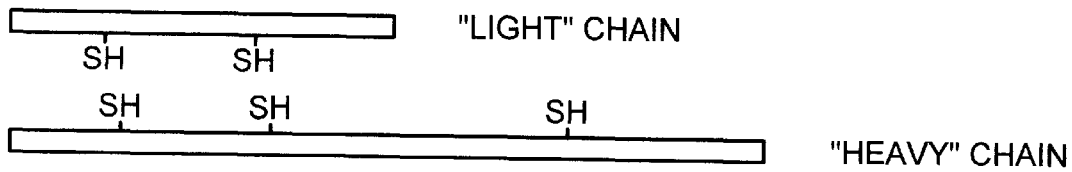

- IN SDS GEL APPROX. 30 kDA, LIGHT CHAIN RUNS
  WITH SOLVENT FRONT AND IS THUS NOT DETACTABLE
- ONLY ONE SEQUENCE

"HEAVY" CHAIN APPROX. 30 kDa
"LIGHT" CHAIN APPROX. 6 kDa
SUM APROX. 36 kDa

STRUCTURE OF PLASMID pKCN2

SEQUENCE LISTING

```
<160> NUMBER OF SEQ ID NOS: 8

<210> SEQ ID NO 1
<211> LENGTH: 1368
<212> TYPE: DNA
<213> ORGANISM: Aspergillus lysophospholipase
<220> FEATURE:
<221> NAME/KEY: intron
<222> LOCATION: (222)..(275)
<220> FEATURE:
<221> NAME/KEY: intron
<222> LOCATION: (442)..(486)
<220> FEATURE:
<221> NAME/KEY: intron
<222> LOCATION: (824)..(874)
<220> FEATURE:
<221> NAME/KEY: CDS
<222> LOCATION: (140)..(220)
<220> FEATURE:
<221> NAME/KEY: CDS
```

-continued

```
<222> LOCATION: (275)..(442)
<220> FEATURE:
<221> NAME/KEY: CDS
<222> LOCATION: (488)..(823)
<220> FEATURE:
<221> NAME/KEY: CDS
<222> LOCATION: (875)..(1180)
<220> FEATURE:
<221> NAME/KEY: mat_peptide
<222> LOCATION: (221)..(1180)
<220> FEATURE:
<221> NAME/KEY: sig_peptide
<222> LOCATION: (140)..(220)

<400> SEQUENCE: 1
atggggaatt gggtggggta atatgataca ggtataaaag ggggctcgga ggtgcagttg      60
gatagaagca ttgtgtgtgc attgcagcag tccgttggtc tcacgtctct ggttgcctcg     120
attgtatata tactgcagg atg ttc tct gga cgg ttt gga gtg ctt ttg aca     172
                    Met Phe Ser Gly Arg Phe Gly Val Leu Leu Thr
                        -25                 -20 gcg ctt gct gcg ctg tgt gct gcg gca ccg aca cca ctt gat gtg cgg     220
Ala Leu Ala Ala Leu Cys Ala Ala Ala Pro Thr Pro Leu Asp Val Arg
    -15                 -10                 -5                  -1 gtaggtgtgc ctgatttgaa gtggctggat agcactgatg aaggttttga atag agt     277
                                                            Ser
                                                              1 gtc tcg act tcc acg ttg gat gag ctg caa ttg ttc tcg caa tgg tct     325
Val Ser Thr Ser Thr Leu Asp Glu Leu Gln Leu Phe Ser Gln Trp Ser
        5                   10                  15 gcc gca gct tat tgc tcg aac aat atc gac tcg gac gac tct aac gtg     373
Ala Ala Ala Tyr Cys Ser Asn Asn Ile Asp Ser Asp Asp Ser Asn Val
            20                  25                  30 aca tgc acg gcc gac gcc tgt cca tca gtc gag gag gcg agc acc aag     421
Thr Cys Thr Ala Asp Ala Cys Pro Ser Val Glu Glu Ala Ser Thr Lys
        35                  40                  45 atg ctg ctg gag ttt gac ctg gtatgttgct ccagtgaaat ggatagaaca         472
Met Leu Leu Glu Phe Asp Leu
50                  55 cagctgattg aatag aca aat aac ttt gga ggc aca gcc ggt ttc ctg gcc    523
                Thr Asn Asn Phe Gly Gly Thr Ala Gly Phe Leu Ala
                                    60                  65 gcg gac aac acc aac aag cgg ctc gtg gtc gcc ttc cga ggc agt agc     571
Ala Asp Asn Thr Asn Lys Arg Leu Val Val Ala Phe Arg Gly Ser Ser
    70                  75                  80 acc atc aag aac tgg att gct gat ctc gac ttc atc ctg caa gat aac     619
Thr Ile Lys Asn Trp Ile Ala Asp Leu Asp Phe Ile Leu Gln Asp Asn
        85                  90                  95                  100 gat gac ctc tgt act ggc tgc aag gtt cac act gga ttc tgg aag gca     667
Asp Asp Leu Cys Thr Gly Cys Lys Val His Thr Gly Phe Trp Lys Ala
                105                 110                 115 tgg gaa gcc gct gca gac aat ctg acg agc aag atc aag tcc gcg atg     715
Trp Glu Ala Ala Ala Asp Asn Leu Thr Ser Lys Ile Lys Ser Ala Met
            120                 125                 130 agc acg tat tcg ggc tat acc ctc tac ttc acc ggg cac agc ttg ggc     763
Ser Thr Tyr Ser Gly Tyr Thr Leu Tyr Phe Thr Gly His Ser Leu Gly
        135                 140                 145 ggc gca ttg gct aca ctg gga gca acg gtc ttg cga aat gac ggt tat     811
Gly Ala Leu Ala Thr Leu Gly Ala Thr Val Leu Arg Asn Asp Gly Tyr
    150                 155                 160 agc gtt gaa ctg gtgagtgctt cagagggtga tcattaaaca gccggttctg         863
Ser Val Glu Leu
165
```

-continued

```
acagtcaata g tac acc tat gga tgt cct cga gtc gga aac tat gcg ctg      913
            Tyr Thr Tyr Gly Cys Pro Arg Val Gly Asn Tyr Ala Leu
                170             175             180 gcc gag cac atc acc agc cag gga tct gga gcg aac ttc cct gtt aca       961
Ala Glu His Ile Thr Ser Gln Gly Ser Gly Ala Asn Phe Pro Val Thr
            185             190             195 cac ttg aac gac atc gtc ccc cgg gtg cca ccc atg gac ttt gga ttc      1009
His Leu Asn Asp Ile Val Pro Arg Val Pro Pro Met Asp Phe Gly Phe
        200             205             210 agc cag cca agt cca gaa tac tgg atc acc agt ggc acc gga gcc agt      1057
Ser Gln Pro Ser Pro Glu Tyr Trp Ile Thr Ser Gly Thr Gly Ala Ser
    215             220             225 gtc acg gcg tcg gat att gaa ctc atc gag gga atc aat tcg acg gcg      1105
Val Thr Ala Ser Asp Ile Glu Leu Ile Glu Gly Ile Asn Ser Thr Ala
230             235             240             245 ggg aat gca ggc gaa gca acg gtg gac gtt ttg gct cac ttg tgg tac      1153
Gly Asn Ala Gly Glu Ala Thr Val Asp Val Leu Ala His Leu Trp Tyr
                250             255             260 ttt ttc gca att tca gag tgt ctg cta tagcttggac agtccgatga            1200
Phe Phe Ala Ile Ser Glu Cys Leu Leu
            265             270 aataagtgcg gagagaaagt gtaaatagta attaagtata tatcaggcag agaagcagtg    1260
gtggtcagag aagaaagagt gagtcccatt acgtagcaga taaccacgtg tggaggcgct    1320
gttcctccac ttgcagttgc ggccatcaat catattcttc tccttact                 1368

<210> SEQ ID NO 2
<211> LENGTH: 297
<212> TYPE: PRT
<213> ORGANISM: Aspergillus lysophospholipase

<400> SEQUENCE: 2

Met Phe Ser Gly Arg Phe Gly Val Leu Leu Thr Ala Leu Ala Ala Leu
        -25                 -20                 -15

Cys Ala Ala Pro Thr Pro Leu Asp Val Arg Ser Val Ser Thr Ser
    -10                 -5              -1   1               5

Thr Leu Asp Glu Leu Gln Leu Phe Ser Gln Trp Ser Ala Ala Tyr
                10              15                  20

Cys Ser Asn Asn Ile Asp Ser Asp Ser Asn Val Thr Cys Thr Ala
                25                  30              35

Asp Ala Cys Pro Ser Val Glu Glu Ala Ser Thr Lys Met Leu Leu Glu
            40                  45              50

Phe Asp Leu Thr Asn Asn Phe Gly Gly Thr Ala Gly Phe Leu Ala Ala
    55                  60                  65

Asp Asn Thr Asn Lys Arg Leu Val Ala Phe Arg Gly Ser Ser Thr
70                  75                  80              85

Ile Lys Asn Trp Ile Ala Asp Leu Asp Phe Ile Leu Gln Asp Asn Asp
                90                  95              100

Asp Leu Cys Thr Gly Cys Lys Val His Thr Gly Phe Trp Lys Ala Trp
            105                 110                 115

Glu Ala Ala Ala Asp Asn Leu Thr Ser Lys Ile Lys Ser Ala Met Ser
        120                 125                 130

Thr Tyr Ser Gly Tyr Thr Leu Tyr Phe Thr Gly His Ser Leu Gly Gly
    135                 140                 145

Ala Leu Ala Thr Leu Gly Ala Thr Val Leu Arg Asn Asp Gly Tyr Ser
150                 155                 160                 165
```

-continued

```
Val Glu Leu Tyr Thr Tyr Gly Cys Pro Arg Val Gly Asn Tyr Ala Leu
            170                 175                 180

Ala Glu His Ile Thr Ser Gln Gly Ser Gly Ala Asn Phe Pro Val Thr
            185                 190                 195

His Leu Asn Asp Ile Val Pro Arg Val Pro Pro Met Asp Phe Gly Phe
            200                 205                 210

Ser Gln Pro Ser Pro Glu Tyr Trp Ile Thr Ser Thr Gly Ala Ser
        215                 220                 225

Val Thr Ala Ser Asp Ile Glu Leu Ile Glu Gly Ile Asn Ser Thr Ala
230                 235                 240                 245

Gly Asn Ala Gly Glu Ala Thr Val Asp Val Leu Ala His Leu Trp Tyr
                250                 255                 260

Phe Phe Ala Ile Ser Glu Cys Leu Leu
            265                 270

<210> SEQ ID NO 3
<211> LENGTH: 27
<212> TYPE: PRT
<213> ORGANISM: Aspergillus lysophospholipase

<400> SEQUENCE: 3

Met Phe Ser Gly Arg Phe Gly Val Leu Leu Thr Ala Leu Ala Ala Leu
1               5                   10                  15

Cys Ala Ala Ala Pro Thr Pro Leu Asp Val Arg
                20                  25

<210> SEQ ID NO 4
<211> LENGTH: 56
<212> TYPE: PRT
<213> ORGANISM: Aspergillus lysophospholipase

<400> SEQUENCE: 4

Ser Val Ser Thr Ser Thr Leu Asp Glu Leu Gln Leu Phe Ser Gln Trp
1               5                   10                  15

Ser Ala Ala Ala Tyr Cys Ser Asn Ile Asp Ser Asp Asp Ser Asn
                20                  25                  30

Val Thr Cys Thr Ala Asp Ala Cys Pro Ser Val Glu Glu Ala Ser Thr
            35                  40                  45

Lys Met Leu Leu Glu Phe Asp Leu
        50                  55

<210> SEQ ID NO 5
<211> LENGTH: 112
<212> TYPE: PRT
<213> ORGANISM: Aspergillus lysophospholipase

<400> SEQUENCE: 5

Thr Asn Asn Phe Gly Gly Thr Ala Gly Phe Leu Ala Ala Asp Asn Thr
1               5                   10                  15

Asn Lys Arg Leu Val Val Ala Phe Arg Gly Ser Ser Thr Ile Lys Asn
                20                  25                  30

Trp Ile Ala Asp Leu Asp Phe Ile Leu Gln Asp Asn Asp Asp Leu Cys
            35                  40                  45

Thr Gly Cys Lys Val His Thr Gly Phe Trp Lys Ala Trp Glu Ala Ala
        50                  55                  60

Ala Asp Asn Leu Thr Ser Lys Ile Lys Ser Ala Met Ser Thr Tyr Ser
65                  70                  75                  80

Gly Tyr Thr Leu Tyr Phe Thr Gly His Ser Leu Gly Gly Ala Leu Ala
```

-continued

```
                        85                  90                  95
Thr Leu Gly Ala Thr Val Leu Arg Asn Asp Gly Tyr Ser Val Glu Leu
            100                 105                 110

<210> SEQ ID NO 6
<211> LENGTH: 102
<212> TYPE: PRT
<213> ORGANISM: Aspergillus lysophospholipase

<400> SEQUENCE: 6

Tyr Thr Tyr Gly Cys Pro Arg Val Gly Asn Tyr Ala Leu Ala Glu His
 1               5                  10                  15

Ile Thr Ser Gln Gly Ser Gly Ala Asn Phe Pro Val Thr His Leu Asn
            20                  25                  30

Asp Ile Val Pro Arg Val Pro Pro Met Asp Phe Gly Phe Ser Gln Pro
            35                  40                  45

Ser Pro Glu Tyr Trp Ile Thr Ser Gly Thr Gly Ala Ser Val Thr Ala
        50                  55                  60

Ser Asp Ile Glu Leu Ile Glu Gly Ile Asn Ser Thr Ala Gly Asn Ala
65                  70                  75                  80

Gly Glu Ala Thr Val Asp Val Leu Ala His Leu Trp Tyr Phe Phe Ala
                85                  90                  95

Ile Ser Glu Cys Leu Leu
            100

<210> SEQ ID NO 7
<211> LENGTH: 42
<212> TYPE: DNA
<213> ORGANISM: Aspergillus lysophospholipase

<400> SEQUENCE: 7
ggaattcacc tgctaaccat gttctctgga cggtttggag tg                              42

<210> SEQ ID NO 8
<211> LENGTH: 34
<212> TYPE: DNA
<213> ORGANISM: Aspergillus lysophospholipase

<400> SEQUENCE: 8
cgggatccaa gctatagcag acactctgaa attg                                       34
```

PROTEIN WITH PHOSPHOLIPASE ACTIVITY

This invention relates to a protein having phospholipase activity which has the mature sequence of Aspergillus lysophospholipase or a sequence derived therefrom and which may be cleaved at at least one site, wherein the restriction fragments are optionally either linked by means of at least one bond cleavable under reducing conditions or at least one of the unlinked restriction fragments has phospholipase activity. The invention furthermore relates to a process for the production of this protein and to the use of this protein for degumming vegetable oils and as a baking auxiliary.

When degumming edible oil, non-hydratable phospholipids are rendered water soluble by phospholipase and thus removed from the edible oil gently, at low cost and in an environmentally friendly manner. European patent application 0 513 709 (Röhm/Lurgi) for the first time presents an effective enzymatic degumming process. In this process, an edible oil, previously degummed with water, is emulsified with an aqueous solution of a phospholipase to yield droplets smaller than 10 μm. After hydrolysis (pH 3 to 6, temperature 50 to 70° C.), the aqueous phase is separated. Lurgi has introduced this enzymatic degumming process into the edible oils industry as the "EnzyMax process". DE 43 39 556 describes a further variant of this process involving reuse of the enzyme by dissolving the enzyme out of a spent aqueous phase containing gum by adding surfactants or solubilising agents and reusing it as a substantially gum-free solution containing enzyme.

Producing sufficient quantities of enzyme for operating the process on a large industrial scale is possible only by using microorganisms. There is thus a requirement for a microbial source which allows production of unlimited quantities of the enzyme phospholipase. DE-OS 195 27 274.9 (Rbhm/Lurgi), dated 26.07.1995, states that a suitable phospholipase has been found in *Aspergillus niger*. This phospholipase cleaves lecithin to lysolecithin, but is also capable of cleaving lysolecithin further to yield phosphatidylcholine. Pure lysophospholipases from Aspergillus which are only capable of cleaving lysolecithin are ineffective in the degumming process. This also applies to the non-acyl-cleaving phospholipases C and D.

Phospholipases may furthermore be used as baking auxiliaries to improve dough processing.

The object underlying the present invention is to provide a low-cost phospholipase at elevated purity. It should be possible to produce the phospholipase in large quantities by means of a transformed host organism. Using the enzyme, it should be possible to produce preparations which are particularly suitable for hydrolysing phospholipids and thus for clarifying starch hydrolysates and for producing baking auxiliaries.

This object is achieved according to the invention by a protein having phospholipase activity, which is characterised in that it has the mature sequence of the Aspergillus lysophospholipase or a sequence derived therefrom and it may be cleaved at at least one site, wherein, in the event of cleavage, the restriction fragments are either linked by means of at least one bond cleavable under reducing conditions or at least one of the unlinked restriction fragments has phospholipase activity. This object is furthermore achieved by a protein having phospholipase activity, which is characterised in that it is recognised by an antibody against purified phospholipase from *Aspergillus foetidus* RH 3046.

It has surprisingly been found that a microorganism transformed with the deoxyribonucleic acid (DNA) isolatable from Aspergillus according to DE-OS 196 20 649.9 does not merely code for a lysophospholipase, but, under certain culture conditions, also continues processing to yield a phospholipase. The phospholipase thus has the same primary structure as the lysophospholipase, but a different secondary and tertiary structure and thus different physiological properties. The corresponding sequence is represented in SEQ ID no. 1 of DE-OS 196 20 649.9. Another phospholipase coding sequence has been isolated from *Aspergillus niger*, only 6% of the amino acids of which differ from the homologous sequence from *Aspergillus foetidus*. Both the phospholipase from *Aspergillus niger* and the lysophospholipase from *Aspergillus foetidus* consist of 270 amino acids and have molecular weight of 36000 Da (c.f. SEQ ID no. 1+2). Reference is made to the disclosure of DE-OS 196 20 649.9 with regard to obtaining the transformed microorganisms. No phospholipase from Aspergillus has hitherto been described in the prior art. The paper by Nakaya et al., *Eur. J. Biochem.* 1990, 193 (1) 31–38 describes a protein having a sequence similar to phospholipase A2.

Phospholipase could be separated from lysophospholipase and obtained at elevated purity using protein chemistry methods. Comparison of the purified phospholipase and lysophospholipase revealed the following differences:

The molecular weights of phospholipase and lysophospholipase from *Aspergillus foetidus*, measured by SDS gel electrophoresis under reducing conditions are approx. 30000 Da for phospholipase and approx. 36000 Da for lysophospholipase, while under non-reducing conditions they are identical for both enzymes at approx. 36000 Da. Under reducing conditions, the phospholipase decomposes into two chains, the larger of which (30000 Da) is retained in the electrophoresis gel. For methodological reasons, the fragment of a size of approx. 6000 Da cannot be detected in the same electrophoresis gel, but it may be deduced from this finding that phospholipase consists of two peptide chains. This view is confirmed by the results of the protein sequencing.

Protein sequencing of the phospholipase from *Aspergillus foetidus* revealed a great degree of homology with the lysophospholipase sequence, but also differences. In phospholipase, two $NH_2$ terminal groups were found in a 1:1 ratio, while only one was found in lysophospholipase. One of the two $NH_2$ terminal groups of the phospholipase belongs to a 6000 Da peptide, while the other is the $NH_2$ terminal group of the 30000 Da protein. While the smaller peptide matches with amino acids 1 to 44 of the mature lysophospholipase protein (c.f. sequence ID no. 1 in DE-OS 196 20 649.9), the sequence of the 30000 Da protein corresponds to amino acids 45 to 270 of the lysophospholipase (c.f. sequence ID no. 1 in DE-OS 196 20 649.9).

This finding makes it clear that the phospholipase from *Aspergillus foetidus* may be obtained by processing the lysophospholipase protein, wherein it has yet to be clarified whether processing proceeds inside or outside the cell and how the processing proceeds. The relationships between phospholipase and lysophospholipase are shown in FIG. 1.

Phospholipase and lysophospholipase furthermore differ in their isoelectric points, their pH and temperature optima and very distinctly with regard to temperature stability.

These parameters are compared in the following table.

TABLE 1

Comparison of the properties of phospholipase and lysophospholipase from *Aspergillus foetidus*

|  | Phospholipase | Lysophospholipase |
|---|---|---|
| Molecular weight (SDS gel, reducing) | 30000 Da | 36000 Da |
| Molecular weight (SDS gel, non-reducing) | 36000 Da | 36000 Da |
| Isoelectric point | pH 4.3 | pH 4.2 |
| Temperature optimum | 50° C. | 55° C. |
| pH optimum | pH 3–4 | pH 4.5 |
| pH stability (1 h at 60° C.) | pH 3.5 >75% residual activity | pH 4.5 10% residual activity |

Fermentation conditions are essential to obtaining phospholipase instead of lysophospholipase from the microorganisms concerned. It is essential to perform culturing in an acidic to slightly alkaline medium in order to form the phospholipase. A suitable pH value for this purpose is in the range from 2 to 9, preferably from 3 to 8. Under these conditions, phospholipase is preferentially formed. The following procedure is used:

A suitable host is first of all selected with the aim of achieving the simplest possible production of the phospholipase. Although many species of moulds may be considered as possible hosts, such as for example members of the thermophilic genera Humicola, Thermomyces and Mucor, the genera Rhizopus, Absidia, Chaetomium, Trichoderma, Thielavia, Penicillium and Cephalosporium, it is preferably species of the genus Aspergillus which are used. Once transformed with the plasmids according to the invention, those transformants may be isolated which, in comparison with the hosts, form large quantities of phospholipase. The transformed host organism is preferably an Aspergillus strain of the species *Aspergillus oryzae, Aspergillus sojae, Aspergillus niger, Aspergillus awamori, Aspergillus foetidus, Aspergillus ellipticus, Aspergillus aculeatus, Aspergillus carbonarius* or *Aspergillus phoenicis* or a Trichoderma strain of the species *Trichoderma viride, Trichoderma longibrachiatum* or *Trichoderma reesei.*

A transformant, which is produced by co-transformation of a host strain with a selection plasmid, preferably with pAN7-1, p3SR2 or pSTA10, and an expression plasmid, preferably with pKC3, pKC9, pKC12 or pKCN2, is cultured in a nutrient solution conventional for the host strain, which solution contains at least one metabolisable source of carbon, such as for example maize meal, starch, starch dextrin, and at least one metabolisable organic source of nitrogen, such as for example maize steep liquor, yeast autolysate, soya flour, soya protein or-peptone alone or in combination with inorganic sources of nitrogen such as ammonium salts or nitrates and which, once sterilised, is adjusted to an acidic to slightly alkaline pH value. The nutrient solution may be supplemented by adding substances which particularly promote phospholipase formation. Such substances are present in soya phospholipids, but they also occur in other classes of substances, such as for example polyoxyethylene ethers. Once the sterilised nutrient solution has been inoculated with conidia or vegetative mycelium of the transformant, the transformant grows with aeration at temperatures of between 20° and 60° C., preferably between 25° and 45° C., and produces the phospholipase according to the invention. The pH of the culture is corrected during culturing by addition of acid or base, such that it is maintained in the acidic to slightly alkaline range, preferably between pH 3 and 8. After 48 to 120 hours of culturing, the phospholipase may be recovered by separating the insoluble nutrient solution residues and biomass, which is usually achieved by filtration, and concentrating the filtrate by conventional methods, such as for example by ultrafiltration. The concentrate (retentate) may be used for degumming vegetable oils or for treating phospholipids. The phospholipase may furthermore be used to improve the Theological properties of foodstuffs.

The following microorganisms have been deposited pursuant to the provisions of the Budapest Treaty with Deutsche Sammlung von Mikroorganismen und Zellkulturen (DSM) Mascheroder Weg 1B, 38124 Braunschweig, Germany:

*A. oryzae* RH 3745: accession number DSM 11283 (date of deposit: 11.11.1996)

*A. ellipticus* RH 3886: accession number DSM 11284 (date of deposit: 11.11.1996)

*A. foetidus* RH 3046: accession number DSM 10652 (date of deposit: 24.04.1996)

*E. coli* DH5α pKC3: accession number DSM 10653 (date of deposit: 24.04.1996)

*E. coli* DH5α pKC9: accession number DSM 10654 (date of deposit: 24.04.1996)

*E. coli* DH5α pKC12: accession number DSM 10655 (date of deposit: 24.04.1996)

*E. coli* pKCN2: accession number DSM 11352 (date of deposit: 23.12.1996)

*A. niger* RH 3909: accession number DSM 11353 (date of deposit: 23.12.1996).

The following Examples and Figures illustrate the invention in greater detail.

FIG. 1 shows the processing of the lysophospholipase gene from *Aspergillus* and isolation of the phospholipase.

EXAMPLES

Example 1

Structure of the Expression Vector pKCN2

Figure 2:
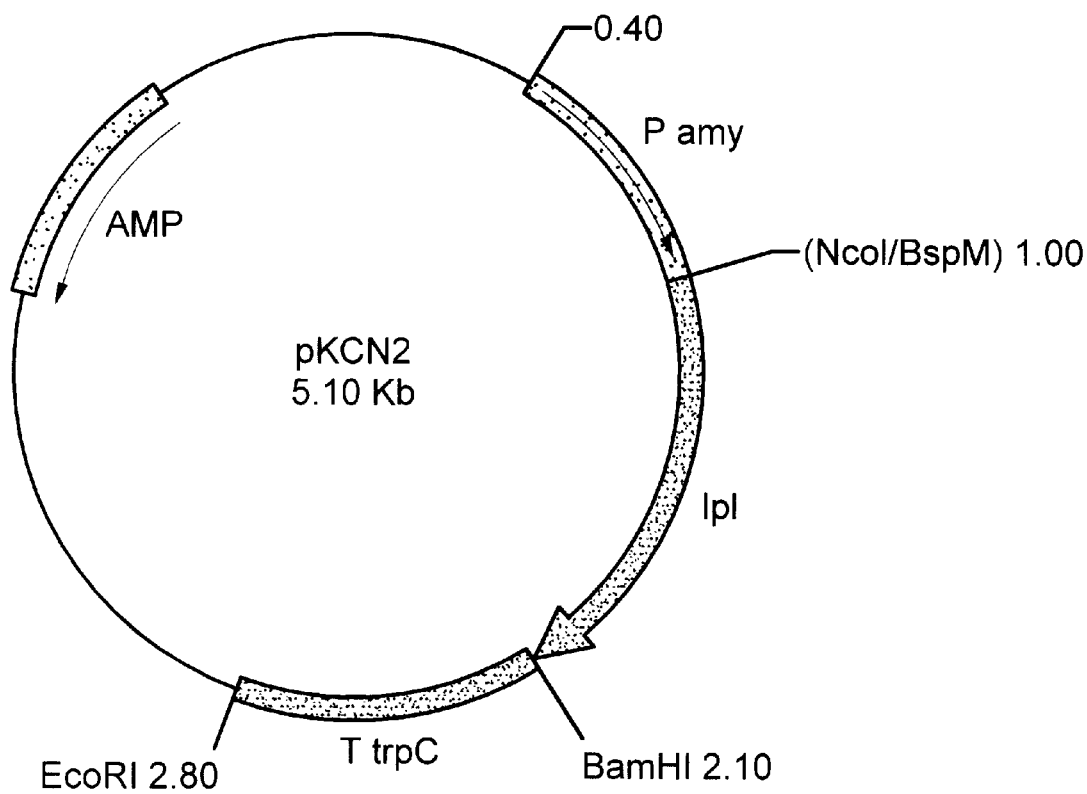
FIG. 2 shows the structure of plasmid pKCN2.

Isolation of the Lysophospholipase Gene from *A. niger* NRRL3

The chromosomal DNA of *A. niger* NRRL3 was isolated using a method described by Hynes, M. J. et al. (1983), *Mol. Cell. Biol.* 3, 1430–1439.

The resultant high molecular weight DNA was partially hydrolysed with Sau3AI and fractionated by size using saccharose density gradient centrifugation. DNA molecules of a size of 9 to 20 kb were inserted in BamHI/EcoRI-hydrolysed EMBL3-DNA and packaged in vitro.

The HindIII/SalI-cDNA fragment from plasmid pKC1/36 was used as a hybridisation probe to identify the chromosomal lysophospholipase gene in a lambda EMBL3 gene library. The plasmid pKC1/36 contained the lysophospholipase cDNA isolated from A. foetidus RH 3046.

After hybridisation and repeated selection, two positive clones could be identified. The phage DNA of clone no. 1 was prepared and digested with BamHI. After Southern hybridisation, it exhibited a positive signal at approx. 9 kb. The BamHI fragment was cloned into pUC18 and the resultant plasmid, which contained the complete chromosomal lysophospholipase gene, was designated PKCN.

Structure of the Expression Vector pKCN2

The lysophospholipase gene in the plasmid pKCN2 was placed under the control of the *A. oryzae* alpha-amylase promoter and the *A. nidulans* trpC terminator.

The lysophospholipase gene was isolated from the plasmid PKCN using the PCR method. Two oligonucleotide primers having the following sequences were used:

```
KC29:
5'-GGA ATT CAC CTG CTA ACC ATG TTC TCT GGA CGG TTT GGA GTG-3'   (SEQ ID no. 3)
          BspMI        Met

KC43:
5'-CG GGATCC AAG CTA TAG CAG ACA CTC TGA AAT TG-3'              (SEQ ID no. 4)
    BamHI          AMB
```

50 mM of KCl, 1.5 mM of $MgCl_2$, 0.2 mM of dNTP (0.2 mM each of dATP, dCTP, dGTP, dTTP), 50 pmol each of KC29 and KC43, 1 ng of pKCN as matrix and 2.5 U of Taq polymerase were mixed together in a reaction volume of 0.1 ml of 20 mM tris/HCl, pH 8.4 for the polymerase chain reaction. The mixture was passed through 20 cycles (94° C., 40 sec; 40° C., 1 min; 72° C., 1 min). On completion of the reaction, the amplified fragment was purified, hydrolysed with BspMI and BamHI and inserted into the plasmid pKE2 cleaved with NcoI/BamHI. The plasmid pKE2 contains the A. oryzae alpha-amylase promoter and the A. nidulans trpC terminator.

The structure of plasmid pKCN2 was confirmed by restriction analysis and subsequent sequencing.

Example 2

Transformation Method for Aspergillus and Trichoderma Reesei Strains

A spore suspension was prepared from an approx. 2 week old Petri dish culture of the fungal strain to be transformed by flotation with the assistance of a spatula in approx. 10 ml of 0.85% NaCl. Four 1 litre shaker flasks each containing 100 ml of Czapek-Dox minimal medium (Oxoid) with 0.1% yeast extract were each inoculated with 1 ml of spore suspension and incubated for approx. 16 hours at 28° C. on an orbital shaker at 120 revolutions per minute. The mycelium from each of the four shaker flasks was harvested in a paper filter and rinsed with approx. 50 ml of MP buffer (1.2 M $MgSO_4$ in 10 mM phosphate buffer, pH 5.8). Once the buffer had drained away, the moist mycelium was weighed. Approx. 3 to 5 g of moist mycelium were generally obtained.

5 ml of MP buffer, 120 μl of Novozym solution (1 g of Novozym® 234 (Novo Nordisk) in 6 ml of MP buffer) and 25 μl of β-glucuronidase (Sigma) were added per g of moist mycelium. The mycelium suspension was placed in iced water for 5 minutes. 60 μl of bovine serum albumin solution (0.2 g of bovine serum albumin in 4 ml of MP buffer, sterile-filtered) were then added and the mixture incubated at 30° C. with gentle shaking. The formation of protoplasts was monitored visually under a microscope. Once no further substantial increase in protoplast formation was discernible, incubation of the mixture was terminated for harvesting of the protoplasts. This generally occurred after some 3 to 5 hours.

The protoplast suspension was passed through a glass wool filter saturated with MP buffer in order to remove any coarse mycelium constituents still present and transferred into centrifuge microtubes. A layer of 600 mM of sorbitol, 100 mM of tris/HCl, pH 7.0 was introduced into the upper half of the microtubes. The microtubes were centrifuged for 10 minutes at 2500 g. The protoplasts were removed from the interlayer and suspended in 1 M sorbitol, 10 mM tris/HCl, pH 7.5. The protoplasts were then washed twice with STC buffer (1 M sorbitol, 10 mM tris/HCl, pH 7.5, 10 mM $CaCl_2$) by centrifugation at 1500 g and finally suspended in 1 ml of STC buffer.

A. oryzae was transformed by combining 300 μl of protoplast suspension, approx. 10 μg of p3SR2 as the selection plasmid and 10 μg of the particular plasmid to express the LPL in 25 μl of 10 mM tris/HCl, pH 8.0, and incubating the mixture for 10 minutes at 0° C. A further 25 μl of the same plasmid mixture and 400 μl of PEG solution (60% polyethylene glycol 6000 (Fluka) in 10 mM tris/HCl, pH 7.5, 50 mM $CaCl_2$) were combined, very carefully mixed in and incubated for 5 minutes at room temperature. A further 600 μl of PEG solution were added, mixed in and the mixture incubated for a further 20 minutes at room temperature. The mixture was mixed at 45° C. with approx. 9 ml of acetamide soft agar (minimal medium containing 10 mM acetamide as the sole source of nitrogen, 1 M saccharose, 0.6 wt. % agar) and divided between four Petri dishes containing the same medium, but with 1.5 wt. % of agar (Oxoid) and additionally 15 mM CsCl. The plates were incubated at 28° C. After 6 to 10 days, rapidly growing colonies (transformants) were reinoculated onto acetamide medium without saccharose, twice purified by means of single spore colonies and finally transferred onto a complete medium, for example potato-dextrose-agar.

Strains of the species A. niger, A. awamori, A. japonicus or A. foetidus may also be transformed with plasmid p3SR2. Preferably, however, transformation was performed with plasmid pAN7-1. Protoplast preparation and the addition of plasmid DNA proceed in a similar manner as described above for plasmid p3SR2. However, instead of adding acetamide soft agar, the entire transformation mixture is added to 100 ml of Czapek-Dox minimal medium (Oxoid) containing 100 μg of hygromycin B/ml, 1.5 wt. % of agar (Oxoid) and 1 M of saccharose, which has been cooled to approx. 45° C., and carefully mixed. The mixture is then placed in 10 ml portions into Petri dishes, into each of which 10 ml of Czapek-Dox minimal medium (Oxoid) containing 1.5 wt. % of agar (Oxoid), but without hygromycin and without saccharose, had been placed as a solid lower layer. Once the upper agar layer has solidified, the Petri dishes are incubated at 30 to 37° C. Hygromycin B-resistant transformants may be subcultured after approx. 3 to 10 days and, in order to test resistance, are transferred onto Czapek-Dox minimal medium (Oxoid) containing 50 μg of hygromycin B/ml and 1.5 wt. % of agar (Oxoid).

A third selection principle is used to transform A. sojae or A. phoenicis, as the strains used of these species both metabolise acetamide and are resistant to hygromycin B. Mutants having a defective nitrate reductase (niaD) gene, i.e. which no longer grow with nitrate as the sole source of nitrogen, are isolated by selection on a nutrient medium containing chlorate (Cove, D. J. (1976) Heredity 36, 191–203). The defect is offset by transformation with plasmid pSTA10 (Unkles, S. E. et al. (1989) Mol. Gen. Genet. 218, 99–104), which bears the intact information for the nitrate reductase gene, such that the transformants grow with nitrate as the sole source of nitrogen, while growth of the non-transformed cells is retarded.

This selection method is equally suitable for other Aspergillus species as well as for *A. sojae*; however, production of the niaD mutants entails additional effort in comparison with exploiting hygromycin B resistance or acetamide metabolisation.

Example 3

Production of PL-secreting Transformants

Transformants of *A. niger*, *A. awamori*, *A. foetidus*, *A. carbonarius* and *A. ellipticus*

Protoplasts of these Aspergillus species were produced by the method described in Example 1 and co-transformed using plasmid pAN7-1 and one of the plasmids pKC3, pKC9, pKC12 or pKCN2. The protoplasts are regenerated by plating the transformation mixture on hygromycin as described above, isolating the transformants from the regeneration plates, purifying and testing them for production of PL in shaking tests using the following nutrient solution

| | |
|---|---|
| maltodextrin | 3.75% |
| maize steep liquor | 3.0% |
| $KH_2PO_4$ | 1.0% |
| $K_2HPO_4$ | 0.7% |
| Triton X-100 | 0.10% |
| in mains water, sterilised for 30 minutes at 121° C. | |

To this end, the biomass is filtered from the shaken cultures and the phospholipase activity (PLU) measured in the culture filtrate. Transformants are distinguished from the host strain by distinctly increased phospholipase activity.

Transformants of *A. oryzae* and *A. aculeatus*

Protoplast preparation and transformation is also performed for these species as described in Example 2. The protoplasts are co-transformed using plasmid p3SR2 and one of plasmids pKC3, pKC9, pKC12 or pKCN2. The protoplasts are regenerated by plating the transformation mixture on nutrient media containing acetamide as the sole source of nitrogen as described above, isolating the transformants from the regeneration plates, purifying and testing them for production of PL in shaking tests using the following nutrient solution

| | |
|---|---|
| maltodextrin | 3.75% |
| maize steep liquor | 3.0% |
| $(NH_4)_2HPO_4$ | 0.5% |
| Triton X-100 | 0.10% |
| in mains water, sterilised for 30 minutes at 121° C. | |

Transformants of *A. sojae* and *A. phoenicis*

The strains *A. sojae* RH 3782 niaD22 and *A. phoenicis* RH 3828 niaD, both of which are mutants prepared according to Cove (1976) of *A. soyae* RH 3782 and *A. phoenicis* RH 3828, are cultured in the following nutrient solution prepared from

| | |
|---|---|
| glucose (Merck) | 2% |
| malt extract (Oxoid) | 0.5% |
| Bacto-peptone (Difco) | 0.025% |
| deionised water | |
| adjust pH value to 5.0; sterilisation: 30 minutes at 121° C. | |

Protoplasts are obtained from the mycelium using the method described in Example 1 and these are co-transformed with pSTA10 as the selection plasmid and one of the plasmids pKC3, pKC9 or pKC12. The protoplasts are regenerated by mixing the transformation mixture with 9 ml of soft agar (osmotically stabilising) consisting of

| | |
|---|---|
| 0.1 M Na phosphate buffer pH 6.0 | 15 ml |
| 1 M saccharose (Merck) | 10.28 g |
| Millipore water to make up to | 29.1 ml |
| agar (Oxoid) | 0.18 g (=0.6%) |
| 30 minutes' sterilisation at 121° C., then sterile addition of | |
| salt solution (7.14.2) | 0.6 ml |
| 1 M $NaNO_3$ solution | 0.3 ml | and dividing the mixture between four Agar plates of identical composition, but prepared with 1% agar. After some 6 to 10 days' incubation at 37° C., the transformants are isolated from the agar plates and purified by plating out on nitrate/saccharose agar. Numerous transformants were obtained by selection and subsequent purification on a nutrient medium containing nitrate as the sole source of nitrogen and tested for PL production in shaken flasks using the following nutrient solution

| | |
|---|---|
| maltodextrin | 3.75% |
| maize steep liquor | 3.0% |
| $KH_2PO_4$ | 1.0% |
| $K_2HPO_4$ | 0.7% |
| Triton X-100 | 1.0% |
| in mains water, sterilised for 30 minutes at 121° C. | |

In addition to transformants which produce no or only small quantities of PL, together with the untransformed host strains, further transformants are also found which exhibit distinctly increased PL activity in the culture filtrate. These strains, designated as co-transformants, are suitable for production of the enzyme. Table 2 compares typical PL formation results by transformants and by the untransformed hosts.

TABLE 2

Comparison of PL formation of host strains and transformants.

| Strain or transformant | Relative PL activity |
|---|---|
| *A. oryzae* RH 3745 | 100 |
| *A. oryzae* RH 3745 p3SR2 pKC9 | 3000–4000 |
| *A. oryzae* RH 3745 p3SR2 pKCN2 | 2000–2500 |
| *A. sojae* RH 3782 niaD22 | 100 |
| *A. sojae* RH 3782 niaD22 pSTA10 pKC9 | 500–700 |
| *A. foetidus* RH 3046 | 100 |
| *A. foetidus* RH 3046 pAN7-1 pKC9 | 1000–1500 |
| *A. phoenicis* RH 3828 niaD | 100 |
| *A. phoenicis* RH 3828 niaD pSTA10 pKC9 | 400–600 |
| *A. ellipticus* | 100 |
| *A. ellipticus* pAN7-1 pKC12 | 800–900 |

TABLE 2-continued

Comparison of PL formation of host strains and transformants.

| Strain or transformant | Relative PL activity |
|---|---|
| A. heteromorphus niaD | 100 |
| A. heteromorphus niaD pSTA10 pKC9 | 900–1000 |
| A. carbonarius | 100 |
| A. carbonarius pAN7-1 pKC9 | 400–600 |
| A. aculeatus | 100 |
| A. aculeatus p3SR2 pKC9 | 900–1200 |
| A. niger | 100 |
| A. niger pAN7-1 pKC12 | 700–1000 |
| A. awamori | 100 |
| A. awamori pAN7-1 pKC12 | 600–800 |

Example 4

Purification of PL from *A. foetidus*

2080 ml of culture retentate from *A. foetidus* RH 3788 were diluted with 3520 ml of distilled water to reduce electrical conductivity and adjusted to pH 7.0, with 160 ml of 1 M NaOH. The sample had a volume of 5760 ml and a conductivity of 7.8 mS/cm.

In another stage, ion exchange chromatography was performed on DEAE-Fractogel (Merck). To this end, 5760 ml of the enzyme solution were introduced into a DEAE-Fractogel column (height 278 mm, diameter 100 mm) in four portions (each of 1440 ml). The column was flushed with buffer A (20 mM phosphate buffer prepared from $Na_2HPO_4/KH_2PO_4$, pH 7.0+15 mM NaCl). Elution was performed in a continuous gradient from buffer A to buffer B (buffer A+1 M NaCl). Elution was performed at an elution rate of 70 ml/min and 350 ml fractions were collected.

The fractions were tested for the presence of PL. This was achieved by measurement of PL activity. One PL unit is here defined as the quantity of enzyme which, in an aqueous lecithin solution at pH 3.5 and 40° C., brings about a hydrolysis rate of 1 µM/min.

PL activity was measured as follows:

Substrate: 1 g of Epikuron 200 (phosphatidylcholine from Lucas Meyer) +100 g of distilled water +5 ml of 0.32 M $CaCl_2$ solution were homogenised with an Ultra Turrax.

Analysis: 10 ml of substrate were combined with 10 ml of 1% Triton X-100 solution (Fluka) and 5 ml of 0.0033 M citric acid monohydrate solution and maintained at 40° C. for 10 minutes; pH is established at 3.4 to 3.5. 0.1 ml of enzyme solution was added and the mixture incubated for 10 minutes at 40° C. The enzyme concentration in the test mixture should not exceed 2.5 U/g. On completion of the reaction time, the mixture was back-titrated with 0.01 M KOH to pH 10.0, wherein the first 5 ml were added rapidly and then the titration rate was reduced in order to avoid over-titration.

The enzyme was heated to approx. 95° C. for 15 minutes and inactivated to obtain the blank value (BV). After cooling, dilution was performed as for the main value (MV) and the procedure continued as for the main value.

$$\text{Calculation:} = PLU/g, pH\ 3.5 = \frac{MV\ (ml) - BV\ (ml) * 0.01\ M * 1000}{10\ min * 0.1\ ml\ enzyme\ conc.\ g/ml}$$

In patent application 195 27 274.9 of 26.07.1995, phospholipase is stated in lecithase units, LU/g. 1 lecithase unit is here that quantity of enzyme which, at 40° C., pH 8, liberates 1 pM of fatty acid from egg yolk in 1 minute. 1 LU/g, pH 8 corresponds to 108 PLU/g, pH 3.5.

The PL began to elute at approx. 0.11 M NaCl. The fractions containing PL from four runs were combined (8950 ml) and concentrated to a volume of 2570 ml by means of a CH2A concentrator from Amicon, Hollow Fibre cartridge MW 10,000. This sample was stirred together with 782 ml of 3 M ammonium sulphate solution (sample now contains 0.7 M ammonium sulphate).

In the next stage, 3352 ml of sample were introduced into a Phenyl Sepharose 6 fast flow, low substitution column (Pharmacia, height 215 mm, diameter 100 mm). The column was rewashed with buffer C (20 mM phosphate buffer, pH 7.0±0.5 M ammonium sulphate) and eluted with a continuously falling gradient from buffer C to buffer D (20 mM phosphate buffer, pH 7.0). The fractions containing PL were combined (790 ml) and concentrated with the concentrator (as above) and dialysed against buffer D; 150 ml of sample were obtained.

In a further stage, five 30 ml portions of the sample were introduced into a Mono Q (Pharmacia, 6.3 ml) anion exchange chromatography column. The column was flushed with buffer D and elution was performed over a continuous gradient from buffer D to buffer B, with PL beginning to elute at approx. 200 mM NaCl.

The fractions containing PL were combined and dialysed through PD-10 columns (Pharmacia) against buffer E (20 mM phosphate buffer, pH 7.1). The sample had a volume of 24 ml.

Final purification of PL through Mono P HR5/20 (Chromatofocusing)

The 24 ml (see above) were introduced into the Mono P column (height 200 mm, diameter 5 mm). The column was rewashed with buffer E. The sample was eluted with buffer F (Polybuffer 74 from Pharmacia, diluted 1:10 with distilled water and adjusted to pH 4.0 with 1 M HCl). The PL eluted once 13 times the column volume of buffer F had passed through the column.

In SDS gel electrophoresis, the purified protein exhibits a uniform band having a molecular weight of approx. 31000 Dalton. The isoelectric point is approx. pH 4.3. The protein purified in this manner was used for sequencing. The phospholipase isolated in this manner was used to obtain antibodies in rabbits. Immunisation was performed using the standard method described by Harlowe & Lane (ref. Ed Harlowe & David Lane, *Antibodies*, Cold Spring Harbor Laboratory, 1988). The resultant antiserum could be used directly for Western blots (as also described by Harlowe & Lane), where it specifically labelled the phospholipase band.

Example 5

Degumming of Soya Oil 200 g of wet-degummed soya oil having a residual phosphate content of 160 ppm are heated to 40° C. in a round-bottomed flask. 10 g of water containing 20 mg of citric acid and 100 Units of phospholipase are added. The enzyme originates from fermentation of an *Aspergillus niger* transformant which contains the phospholipase structure. Activity is determined at pH 3.5. To this end, 10 ml of 1% phosphatidylcholine (Epikuron 200 from Lucas Meyer), which contains 0.5 ml of 0.32 M $CaCl_2$, are combined with 10 ml of Triton X-100 solution and 5 ml of 0.0033 M citric acid monohydrate and maintained at 40° C. for 10 minutes.

0.1 ml of correspondingly diluted enzyme solution were added and incubated at 40° C. for 10 minutes. The mixture was titrated to pH 10 with 0.01 M KOH solution. The blank value (enzyme solution heated in the mixture at 95° C. for 15 minutes) is deducted and the calculation according to Example 3 performed.

The content of the round-bottomed flask is vigorously dispersed by means of an external centrifugal pump, the flask contents being passed through the pump approx. once per minute. The aqueous phase is present at a particle size of below 1μ. Samples are taken at two hour intervals and tested for their phosphorus content. The following values were obtained:

| Time in hours | 0 | 2 | 4 | 6 | 8 |
|---|---|---|---|---|---|
| Phosphorus content in ppm | 160 | 24 | 12 | 7 | 3 |

In tests in which the stated method was used, but a corresponding quantity of whey protein, i.e. a non-enzymatic commercial protein or lysophospholipase (G-Zyme from Enzyme Biosystems, USA, 1000 lysophospholipase units per 200 ml of soya oil), was added instead of the enzyme preparation, the phosphorus content could not be reduced below 80 ppm.

Example 6

Improvement of Dough Quality

The following baking test was performed with the phospholipase according to the invention. A dough was prepared from 100 parts by weight of flour, 2 parts by weight of salt, 3 parts by weight of baking yeast, 58 to 60 parts by weight of water and 40 to 50 ppm of ascorbic acid (relative to dough weight) in a spiral kneader (manufacturer: Kemper) for 2 minutes at the low level 1 and 6 minutes at the higher level 2. The enzymes and other additives were added to the water before the beginning of kneading. Dough temperature was 230 to 25° C. After resting for 20 minutes, the dough was divided into 350 g portions to produce an open-baked white bread, shaped, proved for 70 minutes or 90 minutes at 32° C. and 80% relative atmospheric humidity and baked for 32 minutes at 230° C. Table 3 shows the bread volume for various enzyme additives. The baking results show that adding phospholipase improves the baked volume and crumb structure of the bread. The dough stabilising action is evident from the good baking results with an extended proving time (90 minutes).

TABLE 3

Baking tests

| Additives/100 g of flour | Baking volume, 70 min proving | % | 90 min proving | % | Pore structure |
|---|---|---|---|---|---|
| No additives | 1000 ccm | 100 | 1050 ccm | 100 | irregular |
| Fungal amylase, 10000 SKB | 1050 ccm | 105 | 1130 ccm | 107 | irregular |
| Fungal amylase, 10000 SKB + phospholipase, 2500 PLU | 1100 ccm | 110 | 1225 ccm | 117 | irregular |
| Fungal amylase, 50000 SKB | 1225 ccm | 122 | 1275 ccm | 121 | irregular |
| Fungal amylase, 50000 SKB + phospholipase, 12500 PLU | 1275 ccm | 128 | 1365 ccm | 130 | regular |
| Fungal xylanase, 12000 UXYL | 1325 ccm | 133 | 1375 ccm | 131 | regular |
| Fungal xylanase, 1200 UXYL + phospholipase, 12500 PLU | 1375 ccm | 138 | 1475 ccm | 140 | regular |

What is claimed is:

1. An isolated two-chain phospholipase cleavage fragment having phospholipase activity but does not possess lysophospholipase activity, wherein the phospholipase cleavage fragment is obtained by cleaving a mature sequence of Aspergillus lysophospholipase of SEQ ID NO:2 into two cleavage fragments that are linked by at least one bond that is cleavable under reducing conditions.

2. The cleavage fragment of claim 1, wherein said cleavage fragment possesses a molecular weight of about 30 kDa.

3. The cleavage fragment of claim 1, wherein said two-chain phospholipase comprises a molecular weight of about 36 kDa.

4. The cleavage fragment of claim 1, wherein said cleavage fragment is produced by cleavage of said mature Aspergillus lysophospholipase protein between residues 44 and 45.

5. The cleavage fragment of claim 1, wherein said cleavage fragment is derived from a mature protein obtained from Aspergillus foetidus having lysophospholipase activity.

6. The cleavage fragment of claim 1, which is isolated from an Aspergillus culture.

7. The cleavage fragment of claim 6, wherein said culture is an Aspergillus foetidus culture.

8. The phospholipase of claim 1 having phospholipase activity and substantially no lysophospholipase activity, which specifically binds to an antibody produced against a purified phospholipase obtained from Aspergillus foetidus RH3046.

9. The polspholisase of claim 1, which comprises a polypeptide containing at least residues 45 to 270 of SEQ ID NO:2.

10. The phosphlipase of claim 4, wherein said cleavage fragment is obtained by cleavage of a protein having SEQ ID NO:2.

* * * * *